(12) United States Patent
Quisenberry et al.

(10) Patent No.: US 8,100,956 B2
(45) Date of Patent: Jan. 24, 2012

(54) METHOD OF AND SYSTEM FOR THERMALLY AUGMENTED WOUND CARE OXYGENATION

(75) Inventors: Tony Quisenberry, Highland Village, TX (US); Niran Balachandran, Lewisville, TX (US)

(73) Assignee: ThermoTek, Inc., Flower Mound, TX (US)

(*) Notice: Subject to any disclaimer, the term of this patent is extended or adjusted under 35 U.S.C. 154(b) by 1146 days.

(21) Appl. No.: 11/801,662

(22) Filed: May 9, 2007

(65) Prior Publication Data

US 2007/0282249 A1    Dec. 6, 2007

Related U.S. Application Data

(60) Provisional application No. 60/798,982, filed on May 9, 2006, provisional application No. 60/852,803, filed on Oct. 19, 2006.

(51) Int. Cl.
*A61F 7/00* (2006.01)
*A61F 5/34* (2006.01)

(52) U.S. Cl. .............................. 607/104; 602/2; 604/23

(58) Field of Classification Search .................... 604/23; 607/104
See application file for complete search history.

(56) References Cited

U.S. PATENT DOCUMENTS

| 773,828 A | 11/1904 | Titus et al. |
| 2,110,022 A | 3/1938 | Kliesrath |
| 2,504,308 A | 4/1950 | Donkle, Jr. |
| 3,014,117 A | 12/1961 | Madding |
| 3,164,152 A | 1/1965 | Vere Nicoll |
| 3,345,641 A | 10/1967 | Jennings |
| 3,367,319 A | 2/1968 | Carter, Jr. |
| 3,608,091 A | 9/1971 | Olson et al. |
| 3,660,849 A | 5/1972 | Jonnes et al. |
| 3,736,764 A | 6/1973 | Chambers et al. |
| 3,738,702 A | 6/1973 | Jacobs |
| 3,744,053 A | 7/1973 | Parker et al. |

(Continued)

FOREIGN PATENT DOCUMENTS

CH    670 541    6/1989

(Continued)

OTHER PUBLICATIONS

U.S. Appl. No. 12/176,084, Overton L. Parish.

(Continued)

*Primary Examiner* — Roy Gibson
*Assistant Examiner* — Kaitlyn Smith
(74) *Attorney, Agent, or Firm* — Winstead PC

(57) ABSTRACT

An oxygenation and temperature thermal therapy and oxygenation treatment pad with a plurality of air chambers is disclosed for treatment of skin wound tissues. The air chambers are filled and released by a valve assembly that may be separate from or integrated within the blanket. The thermal therapy and oxygenation treatment pad includes a fluid bladder for delivering hot and/or cold therapy to a patient in conjunction with oxygenation. The temperature therapy blanket may also include an air bladder for providing compression. Oxygenation is provided subsequent to initial heating in order to promote oxygen absorption by the wound tissues prior to the cooling thereof which facilitates pulling oxygen into the wound tissues. This Abstract is provided to comply with rules requiring an Abstract that allows a searcher or other reader to quickly ascertain subject matter of the technical disclosure. This Abstract is submitted with the understanding that it will not be used to interpret or limit the scope or meaning of the claims.

15 Claims, 5 Drawing Sheets

U.S. PATENT DOCUMENTS

| | | |
|---|---|---|
| 3,744,555 A | 7/1973 | Fletcher et al. |
| 3,862,629 A | 1/1975 | Rotta |
| 3,894,213 A | 7/1975 | Agarwala |
| 4,006,604 A | 2/1977 | Seff |
| 4,013,069 A | 3/1977 | Hasty |
| 4,206,751 A | 6/1980 | Schneider |
| 4,224,941 A * | 9/1980 | Stivala ............................ 604/23 |
| 4,375,217 A | 3/1983 | Arkans |
| 4,402,312 A | 9/1983 | Villari et al. |
| 4,459,468 A | 7/1984 | Bailey |
| 4,459,822 A | 7/1984 | Pasternack |
| 4,503,484 A | 3/1985 | Moxon |
| 4,547,906 A | 10/1985 | Nishida et al. |
| 4,597,384 A | 7/1986 | Whitney |
| 4,660,388 A | 4/1987 | Greene, Jr. |
| 4,741,338 A | 5/1988 | Miyamae |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Horne et al. |
| 4,962,761 A | 10/1990 | Golden |
| 4,979,375 A | 12/1990 | Nathans et al. |
| 4,996,970 A | 3/1991 | Legare |
| 5,044,364 A | 9/1991 | Crowther |
| 5,051,562 A | 9/1991 | Bailey et al. |
| 5,067,040 A | 11/1991 | Fallik |
| 5,080,089 A | 1/1992 | Mason et al. |
| 5,090,409 A | 2/1992 | Genis |
| 5,092,271 A | 3/1992 | Kleinsasser |
| 5,097,829 A | 3/1992 | Quisenberry |
| 5,106,373 A | 4/1992 | Augustine et al. |
| 5,112,045 A | 5/1992 | Mason et al. |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| D354,138 S | 1/1995 | Kelly |
| D357,747 S | 4/1995 | Kelly |
| 5,402,542 A | 4/1995 | Viard |
| 5,405,370 A | 4/1995 | Irani |
| 5,405,371 A | 4/1995 | Augustine et al. |
| 5,407,421 A | 4/1995 | Goldsmith |
| D358,216 S | 5/1995 | Dye |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,496,262 A | 3/1996 | Johnson, Jr. et al. |
| 5,507,792 A | 4/1996 | Mason |
| 5,509,894 A | 4/1996 | Mason et al. |
| 5,528,485 A | 6/1996 | Devilbiss et al. |
| 5,561,981 A | 10/1996 | Quisenberry et al. |
| 5,566,062 A | 10/1996 | Quisenberry et al. |
| D376,013 S | 11/1996 | Sandman et al. |
| 5,578,022 A | 11/1996 | Scherson et al. |
| 5,588,954 A | 12/1996 | Ribando et al. |
| 5,591,200 A | 1/1997 | Cone et al. |
| 5,648,716 A | 7/1997 | Devilbiss et al. |
| D383,546 S | 9/1997 | Amis et al. |
| D383,547 S | 9/1997 | Mason et al. |
| D383,848 S | 9/1997 | Mason et al. |
| 5,662,695 A | 9/1997 | Mason et al. |
| 5,672,152 A | 9/1997 | Mason et al. |
| 5,675,473 A | 10/1997 | McDunn et al. |
| 5,682,748 A | 11/1997 | DeVilbiss et al. |
| 5,689,957 A | 11/1997 | DeVilbiss et al. |
| 5,690,849 A | 11/1997 | DeVilbiss et al. |
| 5,711,155 A | 1/1998 | DeVilbiss et al. |
| D393,073 S | 3/1998 | Downing et al. |
| 5,731,954 A | 3/1998 | Cheon |
| D394,707 S | 5/1998 | Tsubooka |
| 5,755,755 A | 5/1998 | Panyard |
| 5,772,618 A | 6/1998 | Mason et al. |
| 5,782,780 A | 7/1998 | Mason et al. |
| 5,795,312 A | 8/1998 | Dye |
| 5,807,294 A | 9/1998 | Cawley et al. |
| 5,827,208 A | 10/1998 | Mason |
| 5,831,824 A | 11/1998 | McDunn et al. |
| D403,779 S | 1/1999 | Davis et al. |
| D404,490 S | 1/1999 | Tripolsky |
| D405,884 S | 2/1999 | Roper |
| 5,871,526 A | 2/1999 | Gibbs et al. |
| 5,890,371 A | 4/1999 | Rajasubramanian et al. |
| 5,901,037 A | 5/1999 | Hamilton et al. |
| 5,923,533 A | 7/1999 | Olson |
| 5,980,561 A | 11/1999 | Kolen et al. |
| 5,989,285 A | 11/1999 | DeVilbiss et al. |
| 6,007,559 A | 12/1999 | Arkans |
| 6,055,157 A | 4/2000 | Bartilson |
| 6,058,010 A | 5/2000 | Schmidt et al. |
| 6,058,712 A | 5/2000 | Rajasubramanian et al. |
| 6,080,120 A | 6/2000 | Sandman et al. |
| D428,153 S | 7/2000 | Davis |
| D430,288 S | 8/2000 | Mason et al. |
| D430,289 S | 8/2000 | Mason et al. |
| 6,125,036 A | 9/2000 | Kang et al. |
| 6,129,688 A | 10/2000 | Arkans |
| 6,135,116 A | 10/2000 | Vogel et al. |
| 6,176,869 B1 | 1/2001 | Mason et al. |
| 6,238,427 B1 | 5/2001 | Matta |
| 6,260,890 B1 | 7/2001 | Mason |
| 6,270,481 B1 | 8/2001 | Mason et al. |
| 6,295,819 B1 | 10/2001 | Mathiprakasam et al. |
| 6,305,180 B1 | 10/2001 | Miller et al. |
| 6,319,114 B1 | 11/2001 | Nair et al. |
| 6,352,550 B1 | 3/2002 | Gildersleeve et al. |
| 6,358,219 B1 | 3/2002 | Arkans |
| 6,368,592 B1 * | 4/2002 | Colton et al. ................ 424/93.7 |
| 6,436,064 B1 | 8/2002 | Kloecker |
| 6,462,949 B1 | 10/2002 | Parish, IV et al. |
| 6,508,831 B1 | 1/2003 | Kushnir |
| D472,322 S | 3/2003 | Hoglund et al. |
| 6,551,264 B1 | 4/2003 | Cawley et al. |
| D474,544 S | 5/2003 | Hoglund et al. |
| 6,562,060 B1 | 5/2003 | Momtaheni |
| 6,596,016 B1 | 7/2003 | Vreman |
| 6,648,904 B2 | 11/2003 | Altshuler et al. |
| D484,601 S | 12/2003 | Griffiths et al. |
| D484,602 S | 12/2003 | Griffiths et al. |
| 6,660,027 B2 | 12/2003 | Gruszecki et al. |
| 6,667,883 B1 | 12/2003 | Solis et al. |
| 6,675,072 B1 | 1/2004 | Kerem |
| D486,870 S | 2/2004 | Mason |

| Patent/Pub No. | Date | Inventor |
|---|---|---|
| 6,695,823 B1 * | 2/2004 | Lina et al. ............ 604/304 |
| 6,719,713 B2 | 4/2004 | Mason |
| 6,719,728 B2 | 4/2004 | Mason et al. |
| 6,736,787 B1 | 5/2004 | McEwen et al. |
| D492,411 S | 6/2004 | Bierman |
| 6,775,137 B2 | 8/2004 | Chu et al. |
| D496,108 S | 9/2004 | Machin et al. |
| 6,789,024 B1 | 9/2004 | Kochan, Jr. et al. |
| 6,802,823 B2 | 10/2004 | Mason |
| D499,846 S | 12/2004 | Cesko |
| 6,834,712 B2 | 12/2004 | Parish et al. |
| 6,846,295 B1 | 1/2005 | Ben-Nun |
| 6,848,498 B2 | 2/2005 | Seki et al. |
| 6,855,158 B2 | 2/2005 | Stolpmann |
| 6,893,414 B2 | 5/2005 | Goble et al. |
| D506,553 S | 6/2005 | Tesluk |
| 6,935,409 B1 | 8/2005 | Parish IV et al. |
| 6,936,019 B2 | 8/2005 | Mason |
| D510,140 S | 9/2005 | Brown |
| D510,626 S | 10/2005 | Krahner et al. |
| D515,218 S | 2/2006 | McGuire et al. |
| D523,147 S | 6/2006 | Tesluk |
| 7,066,949 B2 | 6/2006 | Gammons et al. |
| 7,081,128 B2 | 7/2006 | Hart et al. |
| D533,668 S | 12/2006 | Brown |
| D551,351 S | 9/2007 | Silva |
| 7,306,568 B2 | 12/2007 | Diana |
| 7,354,411 B2 | 4/2008 | Perry et al. |
| D568,482 S | 5/2008 | Gramza et al. |
| 7,429,252 B2 | 9/2008 | Sarangapani |
| 7,484,552 B2 | 2/2009 | Pfahnl |
| 7,492,252 B2 * | 2/2009 | Maruyama ............ 340/539.26 |
| D601,707 S | 10/2009 | Chouiller |
| D608,006 S | 1/2010 | Avitable et al. |
| D612,947 S | 3/2010 | Turtzo et al. |
| D618,358 S | 6/2010 | Avitable et al. |
| D619,267 S | 7/2010 | Beckwith et al. |
| D620,122 S | 7/2010 | Cotton |
| D625,018 S | 10/2010 | Smith et al. |
| D626,241 S | 10/2010 | Sagnip et al. |
| D626,242 S | 10/2010 | Sagnip et al. |
| D626,243 S | 10/2010 | Sagnip et al. |
| D626,245 S | 10/2010 | Sagnip et al. |
| D627,896 S | 11/2010 | Matsuo et al. |
| D628,300 S | 11/2010 | Caden |
| D630,759 S | 1/2011 | Matsuo et al. |
| 7,871,387 B2 | 1/2011 | Tordella et al. |
| D634,437 S | 3/2011 | Gramza et al. |
| D634,851 S | 3/2011 | Chiang |
| D635,266 S | 3/2011 | Chiang |
| D635,267 S | 3/2011 | Chiang |
| 7,896,910 B2 | 3/2011 | Schirrmacher et al. |
| D636,497 S | 4/2011 | Giaccone |
| D638,950 S | 5/2011 | Janzon |
| D640,380 S | 6/2011 | Tweardy et al. |
| D640,381 S | 6/2011 | Tweardy et al. |
| 2001/0039439 A1 | 11/2001 | Elkins et al. |
| 2002/0116041 A1 | 8/2002 | Daoud |
| 2003/0089486 A1 | 5/2003 | Parish et al. |
| 2003/0089487 A1 | 5/2003 | Parish, IV et al. |
| 2003/0127215 A1 | 7/2003 | Parish, IV et al. |
| 2003/0135252 A1 | 7/2003 | MacHold et al. |
| 2003/0163183 A1 | 8/2003 | Carson |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0099407 A1 | 5/2004 | Parish, IV et al. |
| 2004/0193218 A1 | 9/2004 | Butler |
| 2004/0221604 A1 | 11/2004 | Ota et al. |
| 2004/0260231 A1 | 12/2004 | Goble et al. |
| 2005/0004636 A1 | 1/2005 | Noda et al. |
| 2005/0006061 A1 | 1/2005 | Quisenberry et al. |
| 2005/0033390 A1 | 2/2005 | McConnell |
| 2005/0039887 A1 | 2/2005 | Parish, IV et al. |
| 2005/0070828 A1 | 3/2005 | Hampson et al. |
| 2005/0070835 A1 | 3/2005 | Joshi |
| 2005/0133214 A1 | 6/2005 | Pfahnl |
| 2005/0143797 A1 | 6/2005 | Parish et al. |
| 2005/0177093 A1 | 8/2005 | Barry et al. |
| 2005/0182364 A1 | 8/2005 | Burchman |
| 2005/0256556 A1 | 11/2005 | Schirrmacher et al. |
| 2005/0274120 A1 | 12/2005 | Quisenberry et al. |
| 2005/0284615 A1 | 12/2005 | Parish et al. |
| 2006/0034053 A1 | 2/2006 | Parish et al. |
| 2006/0058714 A1 | 3/2006 | Rhoades |
| 2006/0137181 A1 | 6/2006 | Parish, IV et al. |
| 2006/0241549 A1 * | 10/2006 | Sunnen ............ 604/23 |
| 2006/0282028 A1 | 12/2006 | Howard et al. |
| 2007/0068651 A1 | 3/2007 | Gammons et al. |
| 2007/0112401 A1 | 5/2007 | Balachandran et al. |
| 2007/0118194 A1 | 5/2007 | Mason et al. |
| 2007/0129658 A1 | 6/2007 | Hampson et al. |
| 2007/0260162 A1 | 11/2007 | Meyer et al. |
| 2007/0282249 A1 | 12/2007 | Quisenberry |
| 2008/0058911 A1 | 3/2008 | Parish et al. |
| 2008/0064992 A1 | 3/2008 | Stewart et al. |
| 2008/0071330 A1 | 3/2008 | Quisenberry |
| 2008/0132976 A1 | 6/2008 | Kane et al. |
| 2008/0249559 A1 | 10/2008 | Brown et al. |
| 2009/0069731 A1 | 3/2009 | Parish et al. |
| 2009/0109622 A1 | 4/2009 | Parish et al. |
| 2009/0149821 A1 | 6/2009 | Scherson et al. |
| 2010/0030306 A1 | 2/2010 | Edelman et al. |
| 2010/0081975 A1 | 4/2010 | Avitable et al. |
| 2010/0137764 A1 | 6/2010 | Eddy |
| 2010/0145421 A1 | 6/2010 | Tomlinson et al. |
| 2010/0249679 A1 | 9/2010 | Perry et al. |
| 2011/0009785 A1 | 1/2011 | Meyer et al. |
| 2011/0071447 A1 | 3/2011 | Liu et al. |
| 2011/0082401 A1 | 4/2011 | Iker et al. |
| 2011/0087142 A1 | 4/2011 | Ravikumar et al. |

FOREIGN PATENT DOCUMENTS

| | | |
|---|---|---|
| DE | 35 22 127 | 1/1987 |
| EP | 0 489 326 | 6/1992 |
| GB | 2373444 A | 9/2002 |
| SU | 689674 | 10/1979 |
| WO | WO-93/09727 | 5/1993 |
| WO | WO-00/40186 | 7/2000 |
| WO | WO-01/14012 A1 | 3/2001 |
| WO | WO 2005007060 A2 * | 1/2005 |

OTHER PUBLICATIONS

U.S. Appl. No. 12/871,188, Parish et al.
U.S. Appl. No. 12/730,060, Parish et al.
Artikis, T., PCT International Preliminary Report on Patentability as mailed Jul. 29, 2005, (10 pgs.).
Tom Lee, T.Y. et al; "Compact Liquid Cooling System for Small, Moveable Electronic Equipment", IEEE Transactions on Components, Hybrids, and Manufacturing Technology, Oct. 15, 1992, No. 5, pp. 786-793.
Copenheaver, Blaine R., International Search Report for PCT/US2007/022148 as mailed Apr. 2, 2008, 2 pages.
Young, Lee W., "International Search Report" for PCT/US07/08807 as mailed Mar. 3, 2008, (2 pages).
Mahmoud Karimi Azar Daryany, et al., "Photoinactivation of *Escherichia coli* and *Saccharomyces cerevisiae* Suspended in Phosphate-Buffered Saline-A Using 266- and 355-nm Pulsed Ultraviolet Light", Curr Microbiol, vol. 56, 2008, pp. 423-428.
J. Li, et al., "Enhanced germicidal effects of pulsed UV-LED irradiation on biofilms", Journal of Applied Microbiology, 2010, pp. 1-8.
U.S. Appl. No. 12/708,422, Balachandran et al.
Cyro/Temp Therapy Systems; Product News Catalogue; Jobst Institute, Inc., 6 pages (Copyright 1982).
U.S. Appl. No. 13/107,264, May 13, 2011, Quisenberry.
U.S. Appl. No. 12/364,434, Feb. 2, 2009, Quisenberry.
U.S. Appl. No. 13/190,564, Jul. 26, 2011, Quisenberry.
U.S. Appl. No. 29/397,856, Jul. 21, 2011, Quisenberry.
U.S. Appl. No. 29/400,194, Aug. 24, 2011, Quisenberry.
U.S. Appl. No. 29/400,202, Aug. 24, 2011, Quisenberry.
U.S, Appl. No. 29/400,212, Aug. 24, 2011, Quisenberry.
U.S. Appl. No. 29/402,115, Sep. 21, 2011, Quisenberry.

* cited by examiner

METHOD OF AND SYSTEM FOR THERMALLY AUGMENTED WOUND CARE OXYGENATION

CROSS-REFERENCE TO RELATED APPLICATIONS

The present application claims priority from, and incorporates by reference for any purpose the entire disclosure of, U.S. Provisional Patent Application Ser. No. 60/798,982, filed May 9, 2006 and U.S. Provisional Patent Application Ser. No. 60/852,803 filed Oct. 19, 2006. Applicants also cross reference U.S. patent application Ser. No. 10/894,369, filed Jul. 19, 2004 entitled "COMPRESSION SEQUENCED THERMAL THERAPY SYSTEM." This application is also related to, and hereby incorporates by reference, commonly assigned U.S. Pat. Nos. 5,097,829 and 5,989,285.

BACKGROUND OF THE INVENTION

1. Technical Field

The present invention relates to a thermally augmented oxygenation system for wound care and method, and more particularly, but not by way of limitation, to a programmable system adapted for oxygenation of a wound area in conjunction with high thermal contrast modalities, specifically adapted to facilitate the healing process.

2. Description of the Related Art

An important aspect of planned patient treatment is wound care. Medical facilities are constantly in need of advanced technology for the cleaning and treatment of skin wounds. The larger the skin wound, the more serious the issues are of wound closure and infection prevention. The rapidity of the migration over the wound of epithelial and subcutaneous tissue adjacent the wound is thus critical. Devices have been developed and/or technically described which address certain aspects of such wound healing. For example, U.S. Pat. No. 6,695,823 B1 describes a wound therapy device that facilitates wound closure. A vacuum pump is taught for collecting fluids from the wound. WO 93/09727 discloses a solution for wound drainage by utilizing negative pressure over the wound to promote the above references migration of epithelial and subcutaneous tissue over the wound.

Another aspect of wound care is the use of oxygen. The use of oxygen for the treatment of skin wounds has been determined to be very beneficial in certain medical instances. The advantages are multitudinous and include rapidity in healing. For this reason, systems have been designed for supplying high concentration of oxygen to wound sites to facilitate the healing process. For example, U.S. Pat. No. 5,578,022 teaches an oxygen producing bandage and method. One of the benefits cited in U.S. Pat. No. 5,578,022 is the ability to modulate a supply of concentrated hyperbaric oxygen to skin wounds. Although oxygen is beneficial in direct application of predetermined dosages to skin wounds, too much oxygen can be problematic. Oxygen applied to a wound site can induce the growth of blood vessels for stimulating the growth of new skin. Too much oxygen, however, can lead to toxic effects and the cessation of healing of the wound. It would be an advantage, therefore, to maximize the effectiveness of oxygen applied to a wound area by enhancing the absorption rate of oxygen into the skin and tissue fluids. By enhancing the absorption rate of the oxygen in the wound, less exposure time and concomitantly fewer toxic side effects to the endothelial cells surrounding the wound, such as devasculation, occurs. It would be a further advantage, therefore, to utilize existing medical treatment modalities directed toward other aspects of patient therapy to augment oxygenation for wound care.

It has been accepted for many years by medical care providers that patient thermal therapy can be very advantageous for certain injuries and/or post operative recovery. For this reason, thermal therapy has been advanced and many reliable and efficient systems exist today which provide localized thermal therapy to patients in both pre and post surgical environments.

Addressing first thermal therapy systems, several devices have been engineered to deliver temperature controlled fluids through pads or convective thermal blankets to achieve the above purpose. Typically, these devices have a heating or a cooling element, a source for the fluid, a pump for forcing the fluid through the pad or blanket, and a thermal interface between the patient and the temperature controlled fluid. U.S. Pat. No. 4,884,304 to Elkins is, for example, directed to a mattress cover device which contains liquid flow channels which provide the selective heating or cooling by conduction.

Devices have also been developed for simply providing heat or cooling to a person in bed. Electric blankets containing electric heating elements have been used, for example, to provide heat to people in bed. Likewise, cooling blankets, such as the blanket disclosed in U.S. Pat. No. 4,660,388 to Greene, have also been proposed. Greene discloses a cooling cover having an inflatable pad with plenum chambers at opposite ends thereof. Cool air is generated in a separate unit and directed to the pad and out to a number of apertures on the underside of the pad and against the body of the person using the cover.

A disposable heating or cooling blanket is disclosed in U.S. Pat. No. 5,125,238 to Ragan et al., which has three layers of flexible sheeting. Two of the layers form an air chamber while a third layer includes a comfortable layer for contact with the patient. Conditioned air is directed toward the covered person through a multiplicity of orifices in the bottom layers of the blanket.

A temperature controlled blanket and bedding assembly is also disclosed in U.S. Pat. No. 5,989,285 to DeVilbiss et al., assigned to the assignee of the present invention. The disclosure of DeVilbiss discloses a temperature controlled blanket and temperature control bedding system having the provision of both recirculating temperature controlled fluid and temperature controlled gas to enhance performance for convectively heating or cooling a patient. Counter-flow or co-flow heat exchanging principles between the temperature controlled liquid and the temperature controlled gas achieve temperature uniformity across different sections of the blanket and the bedding system. Drapes and the temperature controlled bedding system provided temperature controlled envelope around a person using the bedding system. In one embodiment of the bedding system, the air portion of the bedding system is provided for use with a patient that supplies the fluid portion of the overall bedding system. In another embodiment of the bedding system, the fluid portion of the bedding system is provided for use with a patient bed which supplies the air portion of the overall bedding system.

U.S. Pat. No. 5,097,829 to Quisenberry describes an improved temperature controlled fluid circulating system for automatically cooling a temperature controlled fluid in a thermal blanket with a thermoelectric cooling device having a cold side and a hot side when powered by electricity. The temperature controlled fluid is cooled by the cold side of the cooling device and pumped through, to, and from the blanket through first and second conduits.

Finally, co-pending U.S. patent application Ser. No. 10/894,369 teaches a sequential compression blanket for use with heating or cooling therapy. In this particular embodiment, the utilization of thermal therapy with sequential compression in a programmable format which further has the option of the introduction of oxygenation through a perforated membrane disposed between the patient and the thermal therapy pad is taught. These advances in the medical industry have been recognized as advantageous to both the medical care providers as well as the patients. The precise manner of oxygenation application is, however, still in need of improvement.

The present invention provides improvements in wound care by providing multiple wound healing approaches such as negative pressure over the wound as well as oxygenation in conjunction with thermal therapy. By combining an oxygenation modality that is utilized in conjunction with thermal therapy and/or sequential compression in association therewith, the benefits of both negative wound pressure and oxygenation treatments can be enhanced.

BRIEF SUMMARY OF THE INVENTION

The present invention relates to a method of and apparatus for oxygenation and thermal therapy for wound care. In one aspect, an embodiment of the present invention comprises a compression blanket for use with heating or cooling therapy having an oxygenation region disposed therebeneath providing limited contact to the underlying skin area which may comprise a wound. In this manner, the wound area may receive localized oxygenation and thermal therapy treatment modality.

In another aspect, one embodiment of the invention includes an oxygenation and compression therapy blanket comprising a plurality of gas, such as air, chambers for receiving a gas to cause compression, a valve assembly internal to the compression therapy blanket for delivering gas to each of a plurality of air chambers (which in one embodiment is in a predetermined pattern), an inlet port for delivering air from a control unit to the valve assemblies, and a plurality of connections for delivering gas from the valve assembly to the plurality of gas/air chambers as well as oxygenation gas. The plurality of gas/air chambers may comprise four to seven chambers and an electrical signal connection may be provided for transmitting data related to the predetermined pattern to the valve assembly. One embodiment includes the predetermined pattern comprising sequential inflation of the plurality of chambers to produce series of compression movements peripherally toward a given area of a patient, while another embodiment includes inflating two of the plurality of gas/air chambers simultaneously. The oxygenation is provided via a separate oxygenation gas line which is adapted for filling a localized area on a patient's skin in conjunction with hot and cold therapy.

In yet another aspect, the above described compression therapy blanket further comprises a heat transfer fluid bladder for providing temperature therapy to a portion of a patient to be used in conjunction with oxygenation. The bladder includes a fluid inlet port for delivering heat transfer fluid from the control unit to the heat transfer fluid bladder and a fluid outlet port for delivering heat transfer fluid from the heat transfer fluid bladder to the control unit. The heat transfer fluid bladder delivers thermal treatment to a patient in the form of heat or cold or alternating heat and cold in conjunction with the oxygenation treatment.

Yet a further aspect includes one embodiment of the invention comprising a system for passing heat transfer fluid between a control unit and a blanket in conjunction with oxygenation. The system comprises a reservoir for housing heat transfer fluid for utilization by the system, a flow network in flow communication with the reservoir and including a junction having at least three branches, wherein a first branch receives heat transfer fluid from the reservoir, a second branch receives the heat transfer fluid returning from the blanket, and a third branch for delivering the heat transfer fluid to the blanket, and a pump for creating a low pressure site at the third branch, wherein the low pressure site causes the heat transfer fluid from the second branch to be pulled into the third branch. In one embodiment of the invention, the three-point junction is generally configured as an inverted Y from a fluid flow standpoint. In this particular embodiment, the oxygenation gas would be delivered in a separate line.

In yet another aspect, one embodiment of the invention includes a system for wound cleaning and drainage by negative pressure and then oxygenation of the cleaned and drained wound site in conjunction with thermal therapy comprising a thermal therapy blanket and system for providing heat transfer fluid thereto. The thermal therapy blanket includes at least one spacing member facilitating a separation of a lower surface of the blanket relative to a skin area of the patient for facilitating the receipt of oxygenation gas therein for the treatment of a wound area therebeneath, which wound area is also thermally exposed to the blanket for first heating and opening pores of the skin to expose capillaries and saturate and facilitate the saturation of the skin area with oxygen prior to the cooling thereof which helps close the area and pull oxygen into the underlying tissue. Additionally, one aspect of the invention includes a method of cleaning dead tissue from, and subsequent oxygenation of a wound area in conjunction with thermal therapy wherein thermal therapy-oxygenation treatment pads are held in place by an adhesive border and securing means while oxygenation gasses are fed thereto. In one embodiment, a 93% concentration of oxygen gas is provided at a one to two atmospheric pressure for treatment of the wound site. In one embodiment of the invention, the wound site is warmed through a fluid path on a back side of the treatment pad to five degrees to six degrees above the body temperature to open the pores and expose the capillaries and saturate the area with oxygen for approximately fifteen to thirty minutes.

In another embodiment, the above-described method includes continuing oxygenation at one to two atmospheres while lowering the treatment pad fluid to thirty degrees to forty degrees below body temperature to help close the wound area and pull oxygen into the tissues for a period of time on the order between thirty to forth-five minutes. In another embodiment, the process is repeated periodically with the wound being cleaned of dead tissue by negative pressure, or the like, before each treatment.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF THE INVENTION

Figure 1:
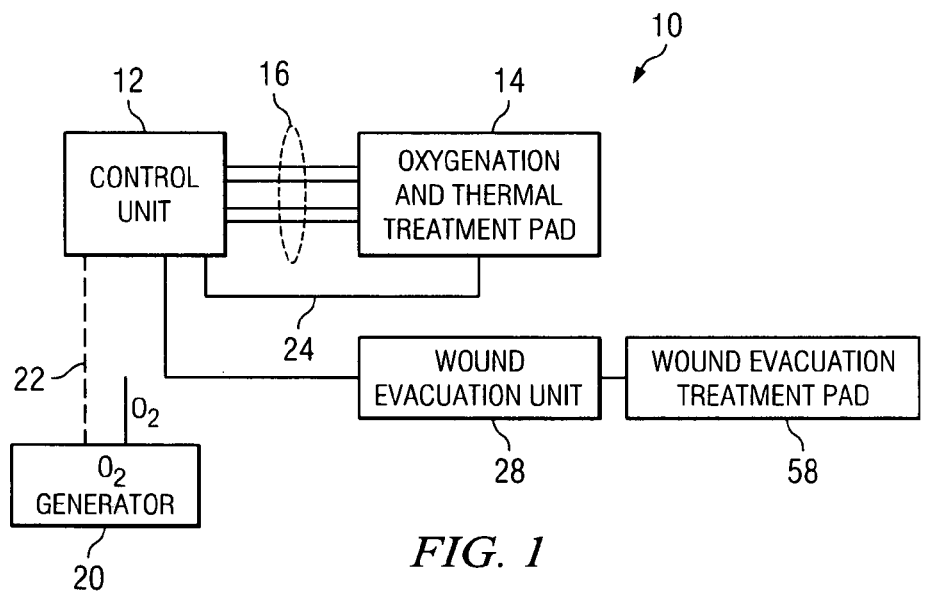
FIG. 1 is an illustration of the oxygenation and thermal therapy system according to an embodiment of the present invention showing both an oxygenation and thermal therapy treatment pad and a second wound evacuation treatment pad.

Referring first FIG. 1, there is shown an illustrations of one embodiment of an oxygenation and thermal therapy system 10 in accordance with the principles of the present invention. The system 10 comprises a control unit 12, a thermal therapy and oxygenation treatment pad 14 and a plurality of tubular members 16 (to be defined below) connecting the control unit 12 to the thermal therapy and oxygenation treatment pad 14. The system 10 further includes a wound evacuation unit 28 and a wound evacuation pad 58 (shown in FIG. 7). The wound evacuation unit 28 is connected to the control unit 12 while the wound evacuation pad 58 is connected to the wound evacuation unit 28. A system for providing both oxygenation therapy in conjunction with certain aspects of thermal therapy and fully describing the thermal operation and sequence compression aspects of one embodiment of the present invention is set forth and shown in parent U.S. patent application Ser. No. 10/894,369 which is incorporated herein in its entirety by reference. For that reason, thermal detail relative to the interaction between the control unit 12 and the thermal therapy and oxygenation treatment pad 14 relative to the thermal fluid flow and pressurization for sequenced compression therapy is not further defined herein. What is defined, is the added aspect of the creation of a localized oxygenation chamber defined by a space disposed beneath an underneath side of the thermal blanket and above the patient's skin. With such a system, oxygen rich gas may be concentrated in an area immediately beneath the thermal therapy and oxygenation treatment pad 14 and substantially contained therebeneath to aid wound healing. The space between the patient's skin and the underneath side of the thermal therapy and oxygenation treatment pad may be defined by attachment edges and other spacer elements which separate the underneath side of the thermal therapy and oxygenation treatment pad 14 from the user's skin or wound site. In this manner, a localized treatment chamber for oxygenation treatment is defined and thermally controlled for maximum efficiency in oxygenation treatment as described below.

Still referring to FIG. 1, the use of the thermal therapy and oxygenation treatment pad 14 to the wound site of the patient may be, in one embodiment, subsequent to the cleaning of the wound area of dead tissue by the wound evacuation pad 58 and the utilization of an adhesive border (in one embodiment) to secure the thermal therapy and oxygenation treatment pad 14 thereover. In one embodiment, Velcro cross straps may be utilized. A 93% concentration of oxygen has been suggested to be advantageous when applied to a wound site as described herein with one or two atmospheres of pressure. In accordance with one aspect of the present invention, an oxygen supply/or an oxygen generator may be utilized within the control unit 12 or may be separate therefrom. In FIG. 1, an oxygen supply and/or generator concentrator 20 is shown in association with the control unit 12 by dotted line 22 and an oxygenation gas line 24 shown extending between the control unit 12 and the thermal therapy and oxygenation treatment pad 14 as a diagrammatic illustration of one embodiment of the principles of the present invention.

Figure 2:
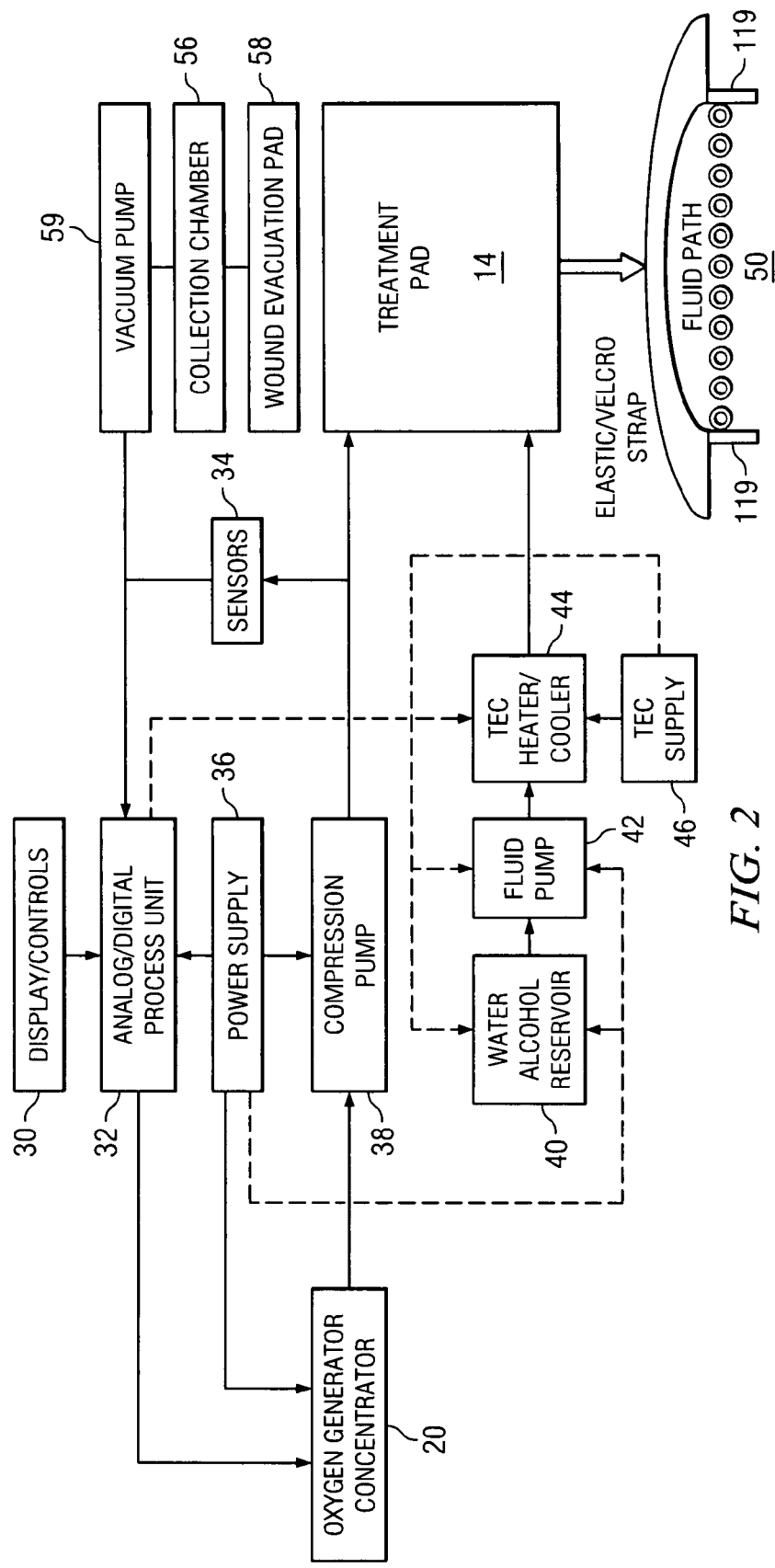
FIG. 2 is a block diagram according to an embodiment of the present invention.

Referring now to FIG. 2, there is a block diagram illustrating the flow of oxygenation gas as a transfer fluid according to an embodiment of the present invention. As set forth in the block diagram, a controlled unit display 30 is provided in conjunction with an analog/digital processing unit 32. The process is referred to herein as "oxytherm" which is the term currently being utilized by the Applicant of the present invention through its assignee in preparation for commercial disclosure of certain ones of the methods, systems and principles of the present invention.

Still referring to FIG. 2, sensors 34 are utilized in conjunction with the digital process unit 32 for control of heat transfer fluids to the thermal therapy and oxygenation treatment pad 14 as well as the oxygen delivery thereto. The oxygen generator concentrator 20 is connected to a power supply 36, which power supply 36, also powers the analog/digital process unit 32. The oxygen generated from the concentrator 20 is then pumped through compression pump 38 before delivery to the thermal therapy and oxygenation treatment pad 14. It should be noted that an oxygen supply may also be used.

Referring still to FIG. 2, a water alcohol reservoir 40 is shown in fluid flow communication with fluid pump 42 and TEC computer cooler 44. The TEC computer cooler 44 is controlled by the digital process unit 32 and a TEC supply 46 is likewise shown. Adjacent the TEC supply 46 is illustrated a diagrammatical schematic of a treatment chamber 50 defined beneath the thermal therapy and oxygenation treatment pad 14 wherein the treatment chamber 50 is thermally exposed to the thermal fluid by the fluid path therein illustrated. The adhesive attachment edges 119 therein shown likewise define the treatment chamber space 50 between the thermal therapy and oxygenation treatment pad 14 and the wound site to allow for the flow of the oxygenation gas therein.

Referring still to FIG. 2, there is shown a vacuum pump 54 powered by the power supply 36. A collection chamber 56 is connected to the vacuum pump 54 and to a wound evacuation pad 58. The wound evacuation pad 58 is used prior to the thermal therapy and oxygenation treatment pad 14, in one embodiment of the present invention, for cleaning the wound area in preparation for oxygenation in conjunction with thermal therapy in accordance with the present invention.

Figure 3:
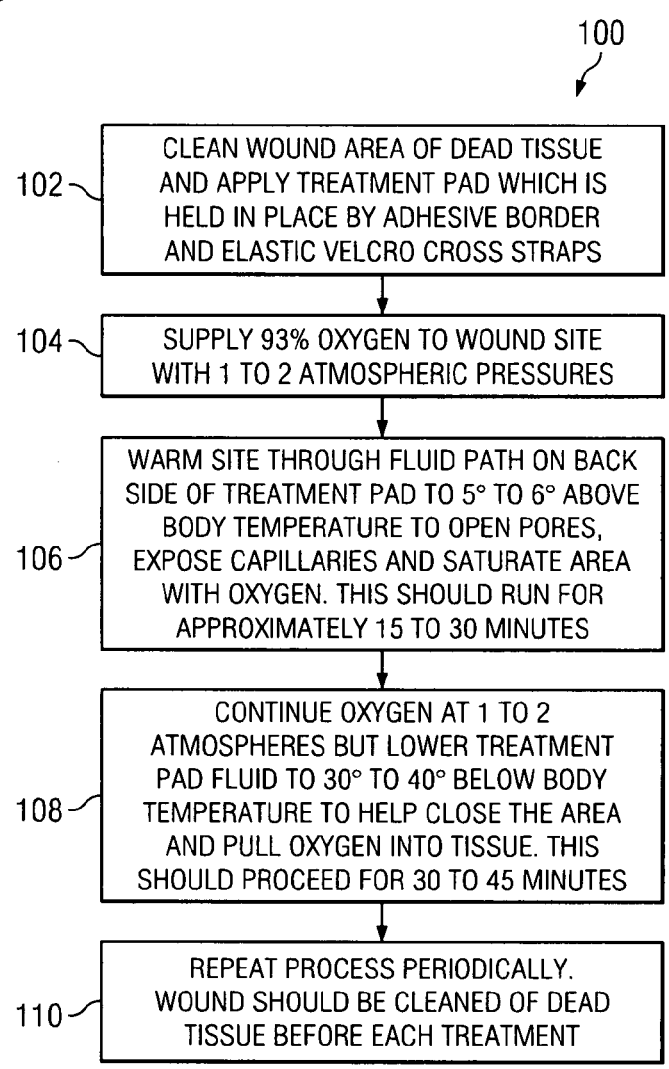
FIG. 3 is a flow diagram listing a process according to an embodiment of the present invention.

Referring now to FIG. 3, there is shown a flow diagram listing a process 100 according to an embodiment of the present invention wherein the wound area is first cleaned of dead tissue and the thermal therapy and oxygenation treatment pad 14 applied in step 102. The thermal therapy and oxygenation treatment pad 14 is held in position by an adhesive border and, in one embodiment, elastic Velcro cross straps. In step 104, a oxygenation gas comprising on the order of 93% concentration of oxygen gas is delivered to the wound site with one to two atmospheric pressures. The numbers are set forth and shown for purposes of reference in that additional studies may be underway relative to the efficacy of other oxygenation concentrations as well as pressures in accordance with the principles of the present invention. The present description is presented as an illustration of the best mode and understanding of the present invention as Applicant is currently aware. Consistent therewith, however, is the concept of, and teachings for, thermal treatment of the wound site in conjunction with the oxygenation and/or cleaning and draining as set forth herein. In accordance therewith, the site is thus warmed through the fluid path herein shown on the back side of the thermal therapy and oxygenation treatment pad 14 up to 5 to 6 degrees above the body temperature of the patient in step 106. This warming allows the pore of the patient's skin to open and expose capillaries therein. The capillaries of the skin are then saturated with oxygen. In one period of time herein described, a period of 15 to 30 minutes is recommended. Oxygenation is continued at one to two atmospheres and the thermal therapy and oxygenation treatment pad fluid is lowered to 30 to 40 degrees below body temperatures to help close the pores of the area and pull oxygen into the underlying tissue in step 108. This step then proceeds for approximately for 30 to 45 minutes in the current embodiment of the present invention. The process is then repeated periodically with the would site cleaned of dead tissue before each treatment in step 110.

Figure 4:
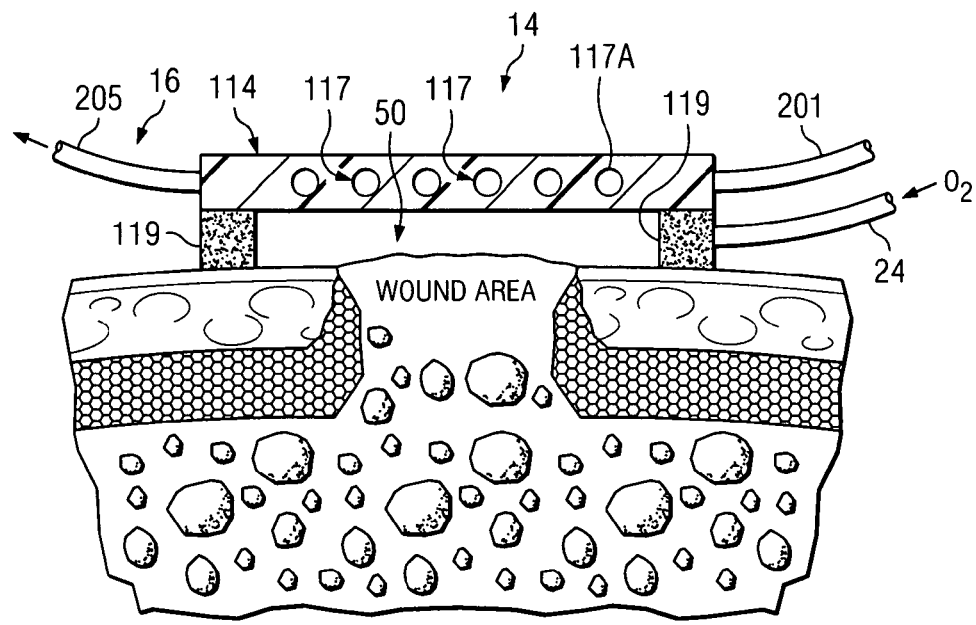
FIG. 4 is a diagram, schematically illustrating in a side elevational cross sectional view a thermal thermal therapy and oxygenation treatment pad according to an embodiment of the present invention.

FIG. 4 is a side elevational, cross sectional view of one embodiment of the thermal therapy and oxygenation treatment pad 14 of the present invention. In this embodiment, the thermal therapy and oxygenation treatment pad 14 is constructed within a single bladder configuration 114 where thermal fluid flow may be provided. The tubes 16 are coupled to the treatment pad 14, which is fabricated with a circuitous flow path therein for thermal fluid flow. This path may be tubular in form, or simply a path within pad 14 defined by flow channels. What is shown is a path 117 within thermal therapy and oxygenation treatment pad 14. The path 117 is shown with tubular ends 117A, for example, in order to illustrate that thermal fluid flows therein for thermal treatment of the underlying wound area. Again, the path 117 may not be of tubular form and may have a variety of shapes and fabrication techniques well know in the art of thermal pads.

Still referring to FIG. 4, a chamber 50 is defined thereby and is separated from the patient's skin by adhesive strips 119 having a thickness (by way of example only) on the order of ⅛ inch. The thermal therapy and oxygenation treatment pad 14 (not drawn to scale) exposes the wound to heat and then cold via path 117 while oxygen is injected into chamber 50. The injection of oxygen in conjunction with the aforesaid heating and cooling via path 117 helps treat the wound and any stasis zones therein where tissue swelling has restricted the flow of blood to the wound tissues. It is well known that without sufficient blood flow the epithelial and subcutaneous tissues referenced above receive less oxygen and are less able to migrate over the wound to promote healing. By utilizing the methods and apparatus of the present invention, oxygenation is enhanced and the problems associated with such conditions mitigated.

Figure 5:
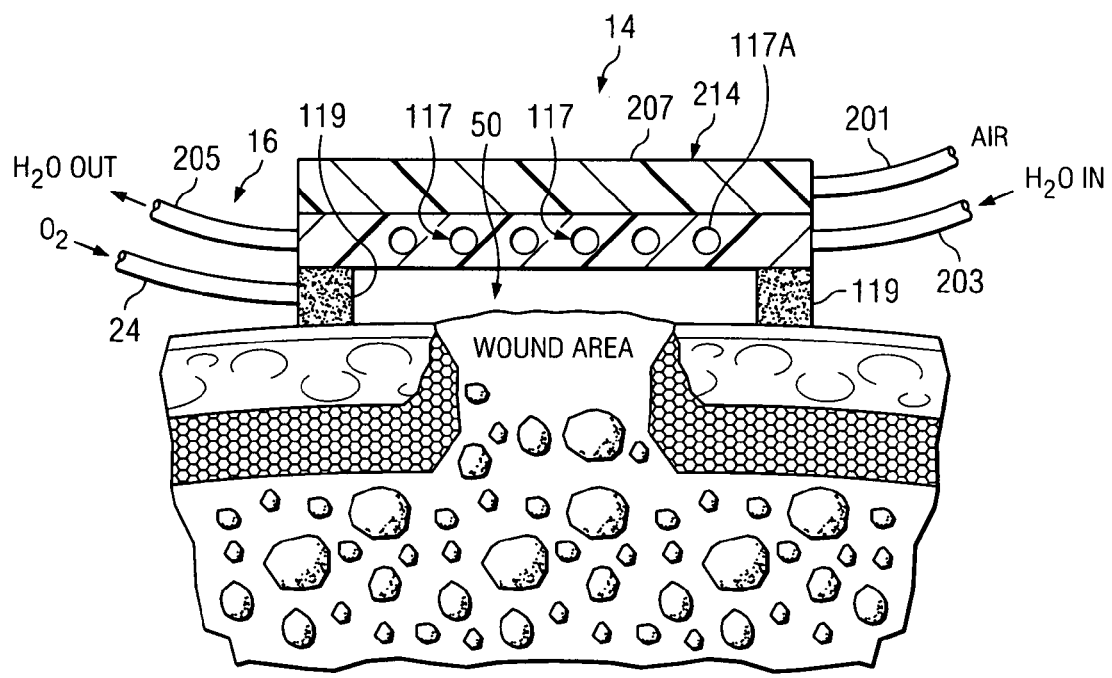
FIG. 5 is a diagram, schematically illustrating in a side elevational cross sectional view a thermal thermal therapy and oxygenation treatment pad according to an alternate embodiment of the present invention wherein compression may be provided.

FIG. 5 illustrates an alternative embodiment of the thermal therapy and oxygenation treatment pad of FIG. 4. A dual bladder configuration 214 is thus provided where air may be applied to bladder 207 atop the thermal flow tubes 117, also represented by the "tubular" ends 117A shown for purposes of example only. In this manner, select compression therapy may be afforded in conjunction with the thermal and oxygenation treatment. In that regard, air inlet tube 201 is illustrated in connection to bladder 207. Both FIGS. 4 and 5 show oxygen tube 24 for feeding oxygen to chamber 50, with tube 203 allowing thermal fluid into conduits 117 with tube 205 allowing thermal fluid return to control unit 12 of FIG. 1.

Figure 6:
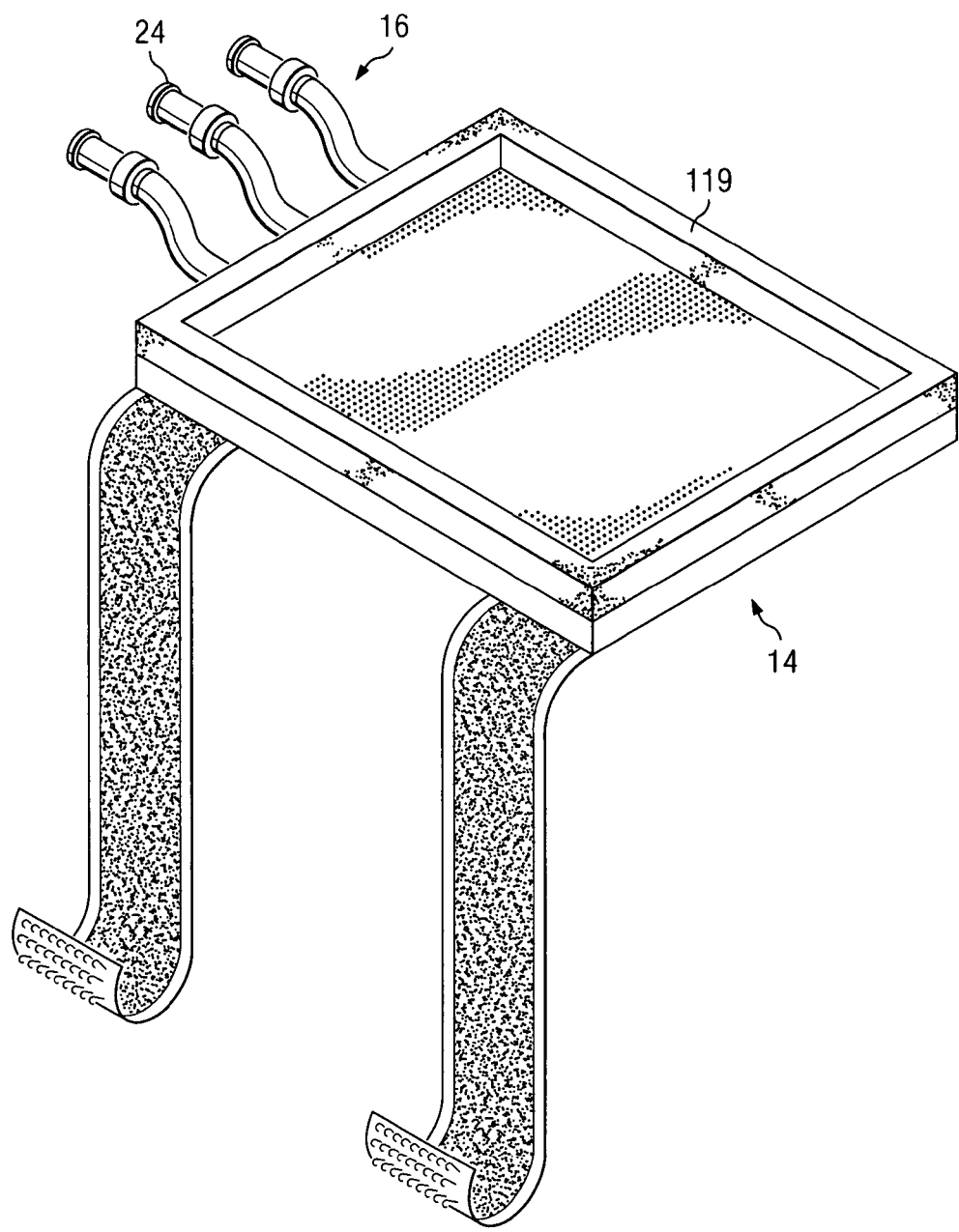
FIG. 6 is a diagrammatic (photographic) illustration of a thermal therapy and oxygenation treatment pad according to an embodiment of the present invention.

Referring now to FIG. 6, there is shown a labeled photographic representation of the thermal therapy and oxygenation treatment pad of FIGS. 1 and 4. The tubular connections 16 for thermal fluid flow and the tube 24 for oxygen flow is clearly seen. The adhesive border 119 is likewise shown, as further outlined for clarity in the photograph of the prototype shown herein.

Figure 7:
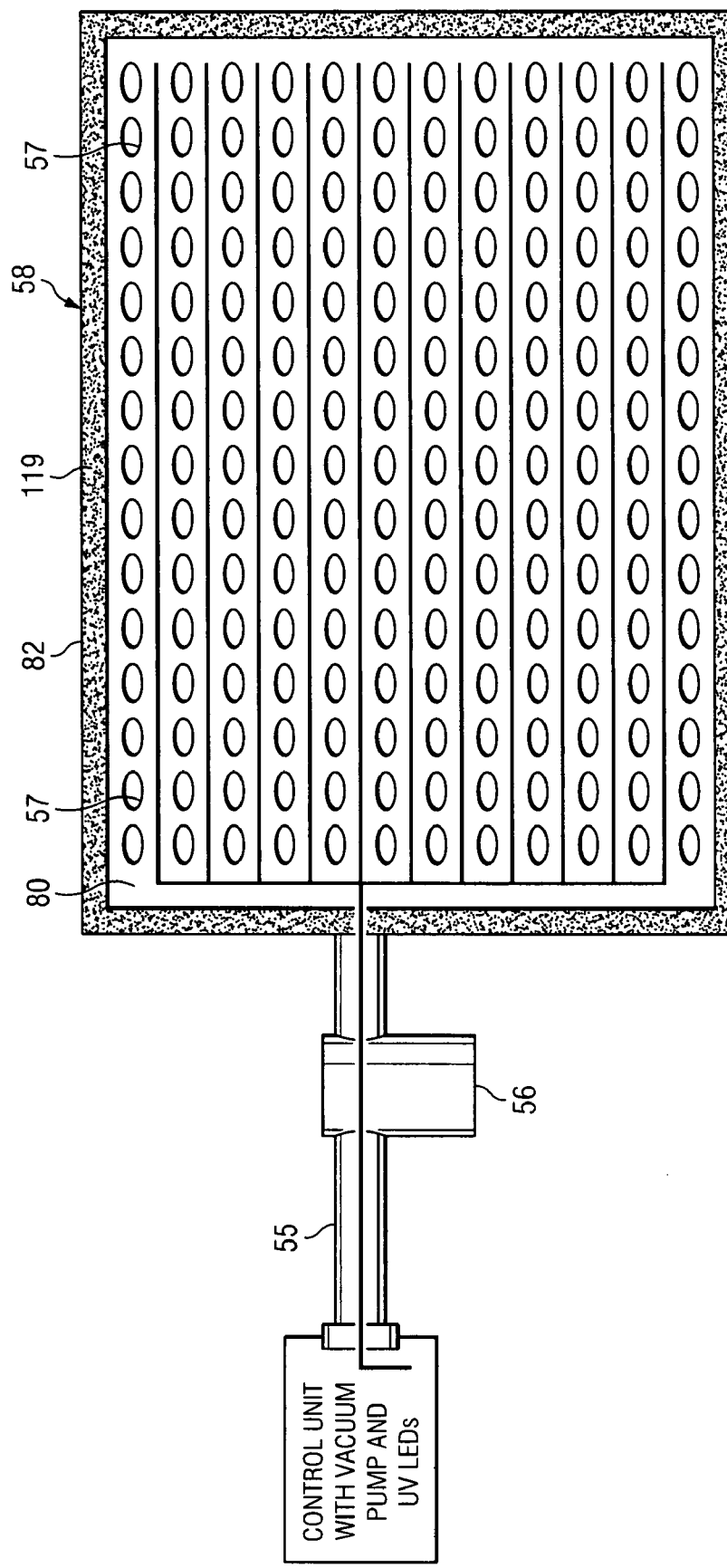
FIG. 7 is a diagrammatic illustration of a wound evacuation pad according to an embodiment of the present invention.

Referring now to FIG. 7, there is shown a diagrammatic illustration of a wound evacuation treatment pad 58. The wound evacuation treatment pad 58 also contains an array of removal ports 57 that may be used to remove any undesirable fluid from the wound area. The wound evacuation treatment pad 58 further contains a non-tissue adhesive surface 80. An adhesive circumference 82 is defined around the periphery of the wound evacuation treatment pad 58 by pads 119 described above to allow for a seal to be formed around the wound area. A similar adhesive may also be used with the treatment pad 14. The seal, in conjunction with the removal ports 57, allows for a negative pressure to form over the wound area, which facilitates the removal of the undesirable tissues from the wound area. The device also includes a control unit 12, which contains a vacuum pump (not shown). The vacuum pump is connected to the wound evacuation treatment pad 58 via a vacuum line 55. A collection chamber 56 is positioned inline between the vacuum pump and the wound evacuation treatment pad 58 to intercept and store any undesirable fluids or the like that are removed from the wound area as a result of applying a negative pressure to the wound area with the vacuum pump. This aspect of one embodiment of the invention is also set forth and shown in U.S. Provisional Patent Application Ser. No. 60/852,803, referenced above, to which priority is claimed.

The previous Detailed Description is of embodiment(s) of the invention. The scope of the invention should not necessarily be limited by this Description. The scope of the invention is instead defined by the following claims and the equivalents thereof.

What is claimed is:

1. A method for wound care utilizing thermal and oxygenation therapies, the method comprising:
   housing, at a reservoir, thermal fluid for utilization by a system;
   providing a treatment blanket in flow communication with the reservoir;
   providing a fluid flow junction having at least three flow branches, wherein a first branch receives thermal fluid from the reservoir, a second branch receives the thermal fluid returning from the treatment blanket, and a third branch for delivering the thermal fluid to the treatment blanket;
   creating a low pressure site at the third branch, wherein the low pressure site causes the thermal fluid from the second branch to be pulled into the third branch;
   cycling between heating and cooling the thermal fluid to provide contrast thermal therapy to a wound of a patient; and
   providing oxygenation therapy concurrently with said cycling for enhancing oxygen absorption by the wound.

2. The method of claim 1, further including providing a heat transfer assembly for heating and cooling the thermal fluid of the third branch.

3. The method of claim 2, wherein providing a heat transfer assembly comprises providing thermoelectric coolers.

4. The method of claim 2, further including pulling the thermal fluid from the reservoir if additional thermal fluid is required by the system.

5. The method of claim 2, further comprising delivering the thermal fluid from the second branch to the reservoir if less thermal fluid is required by the system.

6. The method of claim 2, further comprising providing oxygenation following initiation of thermal fluid to the wound and providing cooling thermal fluid after oxygenation to induce pulling of oxygen into underlying wound tissues.

7. The method of claim 6, further including cleaning the wound prior to oxygenation.

8. The method of claim 7, further comprising cleaning the wound with negative pressure.

9. The method of claim 1, further including providing compression capabilities to the treatment blanket, the compression capabilities comprising:
   providing air from a controller to the treatment blanket; and
   providing a plurality of air chambers within the treatment blanket for receiving the air from the controller.

10. The method of claim 9, further comprising:
    providing a valve assembly for controlling sequencing of the plurality of air chambers; and
    providing air from the controller to the blanket via a single inlet hose.

11. The method of claim 10, further comprising delivering sequencing instructions from the controller to the valve assembly.

12. The method of claim 10, wherein delivering sequencing instructions comprises analyzing a patient profile to determine appropriate sequencing instructions.

13. The method of claim 1, wherein cycling between heating and cooling comprises analyzing a patient wound profile to determine appropriate heating and cooling instructions in conjunction with the oxygenation therapy.

14. The method of claim 13, further comprising delivering the heating and cooling instructions to a heat transfer assembly in conjunction with the oxygenation therapy subsequent to the heating of the wound.

15. A method for utilizing thermal and oxygenation therapies on a wound area of a patient, the method comprising:
    providing a thermal fluid supply and an oxygen supply;
    providing a treatment blanket placed over the wound area, the treatment blanket having an oxygenation chamber disposed beneath an underside of the treatment blanket and above the wound area;
    dispersing thermal fluid from the thermal fluid supply throughout the treatment blanket for heating of the wound area;
    applying heat to the wound area via the thermal fluid;
    directing oxygen from the oxygen supply into the oxygenation chamber for oxygenation therapy of the wound area subsequent to said applying heat; and
    cooling the wound area via the thermal fluid subsequent to said directing.

* * * * *